United States Patent [19]

Katopodis et al.

[11] 4,342,567

[45] Aug. 3, 1982

[54] SIALIC ACID DETERMINATION METHOD

[75] Inventors: Nonda Katopodis, Stanford, Conn.; C. Chester Stock, New York, N.Y.

[73] Assignee: Sloan Kettering Institute for Cancer Research, New York, N.Y.

[21] Appl. No.: 280,616

[22] Filed: Jul. 6, 1981

[51] Int. Cl.$^3$ .......................................... G01N 33/52
[52] U.S. Cl. .................................. 23/230 B; 252/408
[58] Field of Search ...................................... 23/230 B

[56] References Cited

U.S. PATENT DOCUMENTS 4,146,603  3/1979  Davidson .......................... 424/12 X

OTHER PUBLICATIONS

Chemical Abstracts, 84:40392v (1976).

*Primary Examiner*—Sidney Marantz
*Attorney, Agent, or Firm*—Felfe & Lynch

[57] ABSTRACT

A method for determining sialic acid in blood plasma consisting essentially of the steps of precisely diluting the sample and cooling it, extracting with a mixture of chloroform and methanol, adding water to the mixture and separating the phases, adding phosphotungstic acid to the upper layer, centrifuging the resulting mixture and removing the supernatant, suspending the resulting precipitate, adding resorcinol reagent and heating, cooling the reaction mixture and adding butyl acetate-n-butanol to obtain a blue color which can be compared with standard curves to make the determination.

1 Claim, No Drawings

SIALIC ACID DETERMINATION METHOD

BACKGROUND

The present invention relates to an improved method for the determination of lipid bound sialic acid and more particularly to a method which is less time-consuming and requires a much smaller sample than the prior methods.

Much work has been done which indicates that elevated sialic acid content in blood sera of a patient is an indication of the presence of cancer.

Thus, for example, U.S. Pat. No. 4,146,603 to Davidson et al discloses and claims a fairly complex series of procedures whereby elevated sialic acid content is a determinant with respect to cancer specific determinations.

MacBeth and Bekesi, *Cancer Res.* 22, 1170-1176, 1962, measured plasma glycoproteins and found galactose and mannose values were seen in breast cases without metastases. Kloppel et al., 1977, *Proc. Natl. Acad. Sc.* 74, 3011-3013, reported 2.5-fold increases of serum sialic acid glycolipids in mice bearing transplantable mammary carcinomas and 2-fold increases in human carcinoma patients. The method involved column chromatographic separation of the gangliosides. A minimum of 1 ml whole blood was required. Kloppel et al., 1978, *Am. J. Vet. Res.* 39, 1377-1380, also reported increases of sialic acid in 92% of 24 dogs; however, a number of false positive were observed in dogs with other disorders. In leukemic AKR/J mice, Lengle, 1979, *J. Natl. Cancer Inst.* 62, 1565-1567, found increased lipid bound sialic acid in their plasma and thymic lymphocytes. Lipid bound sialic acid levels were found increased in plasma and erythrocytes of humans bearing melanomas (Portoukalian et al., 1978, *Biochem. Biophys. Res. Commun.* 85, 916-920). Chromatographic separation and purification on columns was followed by evaluation on chromatoplates. Silver et al., 1978, *Cancer* 41, 1497-1499; 1979, *Cancer Res.* 39, 5036-5042, have reported elevated serum sialic acid values in melanoma patients that were significantly related to the tumor burden; however, 36% of patients with observable tumors showed no elevated serum sialic acid. Hogan-Ryan et al., 1980, *Br. J. Cancer* 41, 587-592, reporting on total bound serum sialic acid in patients with breast cancer found elevations that corresponded with tumor stage.

The specific method over which the present invention is an improvement is disclosed in the American Association for Cancer Research Annual Meeting PROCEEDINGS Vol 21, March 1980 as Abstract No. 728 by Katopodis et al. Briefly, this method requires that a 100 μl plasma sample (reduced to 50 μl) be extracted with 6 ml of 2 to 1, chloroform to methanol, volume to volume mixture. The lipid extract is then partitioned with 0.2 of its volume of water. The aqueous phase is evaporated to dryness and the residue redissolved in water. The lipid bound sialic acid is then purified by trichloroacetic acid-phosphotungstic acid precipitation and, after the removal of the supernatant from the resultant precipitate, the precipitate is determined by the Svennerholm and Miettien method (Svennerholm, Quantitative Estimation of Sialic Acid . . , *Biochem. Biophys. Acta* 24, pp. 604-611 (1957)).

DESCRIPTION

The present invention avoids the relatively large sample required by the prior art method, eliminates one of the reagents, and is less time-consuming.

More particularly, the inventive procedure requires only about 50 μl of sample rather than the 100 μl required by the prior art method. The drying step is eliminated and there is no use of trichloroacetic acid. Phosphotungstic acid is used alone. In the preferred embodiment, the improved method consists essentially of the following steps.

1. To a screw cap culture tube, 13×100 mm, add 150λ distilled water with a 500λ Hamilton syringe. To this tube transfer a capillary pipette (Unopette, Becton-Dickinson 5841) with its content of 44.7λ of plasma (or serum). Vortex the contents for 5 seconds. Transfer the tube to crushed ice.

2. Add to the tube 3.0 ml cold (4°-5° C.) 2:1 v/v mixture of chloroform and methanol and vortex the mixture for 30 seconds.

3. To this mixture add 0.5 ml cold distilled water, cap the tube and mix the contents by repeatedly inverting the tube for 30 seconds.

4. After centrifuging the tube 5 minutes at room temperature at 2500 rpm, transfer 1 ml of the upper layer into a culture tube like the one already used.

5. Add 50λ phosphotungstic acid solution (1 g/ml) and after mixing let it stand at room temperature for 5 minutes.

6. Centrifuge for 5 minutes at 2500 rpm and remove the supernatant by suction.

7. Add 1 ml water and vortex until the precipitate is in suspension without gross particles (about 1 minute).

8. Add 1 ml of the resorcinol reagent, mix and place the tube in boiling water for exactly 15 minutes.

9. Immediately after the 15 minutes, transfer the tube to an ice and water bath and leave for 10 minutes.

10. To the ice cold tube add 2 ml butyl acetate-n-butanol 85:15 v/v mixture at room temperature, vortex and centrifuge for 5 minutes at 2500 rpm.

11. Read the extracted blue color at 580 nm and the amount of lipid bound sialic acid (LSA) is determined by use of a standard curve developed from a standard sample of n-acetyl neuraminic acid (NANA) and use of this formula:

$$\text{LSA mg/100 ml plasma} = (x \cdot 100{,}000\lambda)/(y \cdot 44.7\lambda \cdot 1000)$$

$x = \gamma$ NANA read from standard curve for the sample
$y = 1$ ml of supernatant ÷ volume of entire supernatant (In our experience this had been 1.00/1.30)

The new procedure was found to give results quite comparable to the prior one. A typical example shows in Table I values for 10 determinations by the new procedure for a sample in which two investigators previously obtained values of 19.3 and 19.5 mg LSA/100 ml plasma by the former procedure. (Katopodis et al, *PROCEEDINGS*, 1980)

TABLE I

| Determination No. | mg LSA/100 ml plasma |
|---|---|
| 1 | 19.6 |
| 2 | 19.3 |
| 3 | 20.0 |
| 4 | 19.0 |
| 5 | 19.3 |

TABLE I-continued

| Determination No. | mg LSA/100 ml plasma |
|---|---|
| 6 | 20.0 |
| 7 | 19.3 |
| 8 | 19.6 |
| 9 | 19.6 |
| 10 | 19.3 |
| Average + S.D. | 19.5 ± 0.3 |

In Table II are shown the results of a representative sampling of values 20 routine hospital admission determinations.

TABLE II

Comparison of LSA values by two proedures

| | LSA mg/100 ml plasma | |
|---|---|---|
| Sample No. | old procedure | new procedure |
| 100 | 18.4 | 18.0 |
| 195 | 29.4 | 29.2 |
| 222 | 14.2 | 14.5 |
| 158 | 22.9 | 22.0 |
| 216 | 21.6 | 21.7 |
| 185 | 17.3 | 16.9 |
| 001 | 53.9 | 54.3 |
| 002 | 18.7 | 19.5 |
| 184 | 14.9 | 13.0 |
| 202 | 18.8 | 19.5 |
| 188 | 36.8 | 36.3 |
| 104 | 15.4 | 15.7 |
| 217 | 18.3 | 18.2 |
| 197 | 16.0 | 16.0 |
| 213 | 24.3 | 24.0 |
| 144 | 20.8 | 21.4 |
| 199 | 22.4 | 21.7 |
| 102 | 20.6 | 20.5 |
| 214 | 25.4 | 24.7 |
| 145 | 20.7 | 19.1 |

In our desire to use small volumes of samples the odd volume of 44.7 was selected only because of the availability of the Becton Dickinson Unopette 5841. More consistent results were obtained when we added the filled Unopette with its contents directly into the extraction tube than when the sample was added by a micropette. Other volumes of this magnitude would be expected to give comparable results.

It was found that the trichloracetic acid could be eliminated in the precipitation step. The 1 g/ml concentration was selected when it was found that 0.25 mg/ml gave somewhat lower values. One-half g/ml gave slightly lower values than 1 g/ml, but they were within the experimental error of the method.

Reextraction of the aqueous portion on step 2 revealed no detectable remaining LSA. This was also true when in step 4 the solvent layer was dried and reextracted with water.

What is claimed is:

1. Method for determining sialic acid in blood plasma or serum, consisting essentially of the steps of:

transferring approximately 50 µl, precisely measured, of serum to a container with 150 µl distilled water; vigorously mixing the container;

cooling the container and contents to about 32° F. (0° C.);

adding to the container 3 ml of cold (4°–5° C.) 2:1 v/v mixture of chloroform and methanol, and mixing vigorously;

adding 0.5 ml cold distilled water to the container and mixing gently;

separating the phases in the container by centrifuging;

adding 50 µl phosphotungstic acid solution (1 gram per ml) to 1 ml of the upper layer from the centrifuge mixture, and mixing;

allowing the phosphotungstic acid solution mixture to stand at room temperature for about 5 minutes;

centrifuging the phosphotungstic acid mixture for 5 mins. at 2500 rpm and removing the supernatant;

adding 1 ml water to the precipitate from which the supernatant has been removed, and mixing well until precipitate is in suspension without gross particles;

adding 1 ml of resorcinol reagent, mixing and placing the container in boiling water for a precise period of time of about 15 minutes;

thereafter transfering the container to an ice and water bath and allowing the contents to cool for about 10 minutes;

to the cold container contents adding 2 ml butyl acetate-n-butanol 85:15 v/v mixture at room temperature, mixing well and centrifuging for 5 minutes at 2500 rpm; and reading the extractive blue color at 580 nm and determining the amount of lipid bound sialic acid by the use of standard curves developed from a standard sample of n-acetyl neuraminic acid (NANA) under the same conditions and by applying the following formula:

LSA mg/100 ml plasma $=(X \cdot 100{,}000\lambda)/(y \cdot 44.7\lambda \cdot 1000)$ $x = \gamma$ NANA read from standard curve for the sample
$y = 1$ ml of supernatant ÷ volume of entire supernatant
(In our experience this had been 1.00/1.30).

* * * * *